United States Patent [19]
Bressel

[11] 3,950,415
[45] Apr. 13, 1976

[54] DECREASING THE AMOUNT OF DICHLOROACETYL CHLORIDE CONTAINED IN MONOCHLOROACETYL CHLORIDE

[75] Inventor: Ulrich Bressel, Mannheim, Germany

[73] Assignee: BASF Aktiengesellschaft, Ludwigshafen (Rhine), Germany

[22] Filed: Mar. 6, 1974

[21] Appl. No.: 448,454

[52] U.S. Cl. .............................................. 260/544 Y
[51] Int. Cl.² ........................................ C07C 53/20
[58] Field of Search .............................. 260/544 Y

[56] References Cited
UNITED STATES PATENTS 3,763,023  10/1973  Haslen ........................... 260/544 Y
3,882,173  5/1975  Bach .............................. 260/544 Y Primary Examiner—Lorraine A. Weinberger
Assistant Examiner—Michael Shippen
Attorney, Agent, or Firm—Johnston, Keil, Thompson & Shurtleff

[57] ABSTRACT

A process for decreasing the amount of dichloroacetyl chloride contained in monochloroacetyl chloride by treating monochloroacetyl chloride containing dichloroacetyl chloride with water, an alcohol or a carboxylic acid followed by separation of monochloroacetyl chloride by distillation from the mixture thus obtained. Monochloroacetyl chloride is used for the production of plant protection agents.

6 Claims, No Drawings

DECREASING THE AMOUNT OF DICHLOROACETYL CHLORIDE CONTAINED IN MONOCHLOROACETYL CHLORIDE

The invention relates to a process for decreasing the amount of dichloroacetyl chloride contained in monochloroacetyl chloride by mixing the latter with certain agents and isolating the monochloroacetyl chloride from the resulting mixture by distillation.

It is difficult to prevent the formation of dichloroacetyl chloride in the production of monochloroacetyl chloride. Since the physical characteristics of monochloroacetyl chloride and dichloroacetyl chloride are very similar, separation of the two compounds by physical methods can only be effected, if at all, with very high expenditure for equipment. When monochloroacetyl chloride is processed into monochloroacetamides which are to be used as plant protection agents the content of dichloroacetyl chloride is deleterious because dichloroacetamides formed therefrom impair biological effectiveness.

It is an object of the invention to provide a process in which by simple distillation in continuous operation and without great expenditure for equipment dichloroacetyl chloride is substantially removed from monochloroacetyl chloride containing the same.

In accordance with this invention this and other objects and advantages are achieved in a process for decreasing the dichloroacetyl chloride content in monochloroacetyl chloride, which comprises treating monochloroacetyl chloride containing dichloroacetyl chloride with water, an alcohol or a carboxylic acid and separating monochloroacetyl chloride by distillation from the mixture thus obtained.

Mixtures which mainly consist of dichloroacetyl chloride and monochloroacetyl chloride are used as a rule as starting materials. They are obtained for example by chlorination of acetyl chloride. It is advantageous to use starting mixtures which contain up to 10% by weight of dichloroacetyl chloride and particularly from 2 to 8% by weight of dichloroacetyl chloride. The starting mixture may also contain small amounts, for example up to 0.5% by weight, of impurities such as acetyl chloride.

The monochloroacetyl chloride containing dichloroacetyl chloride is mixed with water, an alcohol or a carboxylic acid. Suitable alcohols include aliphatic, cycloaliphatic and araliphatic alcohols or phenols of up to ten carbon atoms which contain one or more hydroxyl groups, for example one or two hydroxyl groups, and which may also contain inert substituents, for example alkoxy groups, and which may be unsaturated. Alkanols and alkanediols of up to six carbon atoms and cyclohexanol are preferred. Alkanols of one to four carbon atoms and alkanediols of two to four carbon atoms have acquired particular industrial importance. Examples of suitable alcohols are methanol, ethanol, propanol, butanols, 2-ethylhexanol, octanol, cyclohexanol, benzyl alcohol and phenol and also ethylene glycol, propylene pylene glycol, butyleneglycol-1,2, butyleneglycol-1,4, ethylene glycol monomethyl ether and mixtures of the same, for example with water.

Examples of suitable carboxylic acids are aliphatic, cycloaliphatic and araliphatic and also aromatic carboxylic acids of up to ten carbon atoms which contain one or more than one carboxyl group, for example one or two carboxyl groups. It is preferred to use fatty acids or alkanedicarboxylic acids of up to six carbon atoms. Particular industrial significance attaches to fatty acids of one to four carbon atoms. Examples of suitable carboxylic acids are acetic acid, propionic acid, butyric acid, octanoic acid, glutaric acid, adipic acid, cyclohexanoic acid and benzoic acid.

It is particularly preferred to add water or an alkanol of one to four carbon atoms, particularly methanol, to the monochloroacetyl chloride containing dichloroacetyl chloride.

Water, an alcohol or a carboxylic acid is used as a rule in an amount of from 0.5 to 10% by weight based on the mixture of monochloroacetyl chloride and dichloroacetyl chloride. The amount used depends on the content of dichloroacetyl chloride and should advantageously be equivalent to at least the stoichiometric amount based on dichloroacetyl chloride. It is particularly advantageous to use water, alcohol or carboxylic acid in up to five times the stoichiometric amount based on dichloroacetyl chloride. When water is used it has proved to be suitable not to add such a large amount of water that there is visible formation of hydrogen chloride.

Water, alcohol or carboxylic acid is as a rule added to the mixture of monochloroacetyl chloride and dichloroacetyl chloride prior to distillation. Mixing is usually carried out at ambient temperature so that the mixture is heated up by the added agent, for example to a temperature of from 30°C to 60°C. Mixing may be carried out in stirred vessels or particularly advantageously in a mixing zone having an L:D ratio of from 10:1 to 20:1 in which turbulent flow is maintained. On the other hand it is also possible to add water, alcohol or carboxylic acid to the mixture of dichloroacetyl chloride and monochloroacetyl chloride in the column in which the monochloroacetyl chloride is distilled off. In this case water, alcohol or carboxylic acid may be supplied together with the mixture of monochloroacetyl chloride and dichloroacetyl chloride, or the additive may be introduced at a point below the supply of monochloroacetyl and dichloroacetyl chloride.

The mixture of monochloroacetyl chloride and dichloroacetyl chloride with water, alcohol or carboxylic acid is distilled in a column. As a rule a packed bubble tray column or a sieve plate column is used for the purpose. The distillation is generally carried out at atmospheric pressure or advantageously at subatmospheric pressure, for example at from 50 to 500 mm Hg. The temperature of the column depends on the boiling point of the monochloroacetyl chloride while a temperature of less than 130°C and advantageously of less than 120°C is maintained in the bottoms. It has also proved to be particularly suitable to keep the residence time in the bottoms of the column short. Mean residence times of from ten to sixty minutes have proved to be suitable for example.

When the content of dichloroacetyl chloride is not adequately reduced after a single treatment it is possible to repeat the treatment a number of times in order to achieve the smallest possible content of dichloroacetyl chloride.

Monochloroacetyl chloride having a low content of dichloroacetyl chloride is suitable for the production of chloroacetamides which may be used as plant protection agents (cf. U.S. Pat. No. 3,576,860).

The process according to the invention is illustrated in the following Examples.

EXAMPLE 1

58 g of water is added to 5722 g of chloroacetyl chloride which contains 2.11% by weight of dichloroacetyl chloride. 800 g of the mixture is placed in a distillation flask and distilled in a packed column having a length of 1.5 meters and a diameter of 30 mm with a packing of Raschig rings having a diameter of 3 mm at 100 mm. 600 ml of the mixture prepared is supplied per hour into the upper third of the column through a water-heated preheater and such an amount of monochloroacetyl chloride is distilled off over the top that the level is maintained constant in the distillation flask. A temperature of 51°C is maintained at the top of the column while the temperature in the distillation bottoms rises from 96° to 98°C. A total of 4795 g of monochloroacetyl chloride is obtained which contains 1.40% by weight of dichloroacetyl chloride. 764 g having a content of 7% by weight of dichloroacetyl chloride and dichloroacetic acid remains as distillation bottoms. A depletion of 33.6 percent based on the crude mixture introduced is calculated.

COMPARATIVE EXAMPLE

The procedure described in Example 1 is repeated but 6349 g of chloroacetyl chloride having a content of 2.11% by weight of dichloroacetyl chloride is distilled without adding water. 5243 g of monochloroacetyl chloride is obtained at the top of the column with a dichloroacetyl chloride content of 2.10% by weight.

EXAMPLE 2

The procedure of Example 1 is repeated but a mixture of 6108 g of chloroacetyl chloride having a content of 1.2% by weight of dichloroacetyl chloride and 62 g of water is used. 5211 g of chloroacetyl chloride having a content of 0.78% by weight of dichloroacetyl chloride is obtained at the top of the column. The depletion is 35 percent.

EXAMPLE 3

5038 g of chloroacetyl chloride having a content of 2.6% by weight of dichloroacetyl chloride is carefully mixed with 265 g of water. After cooling crystals of chloroacetic acid separate out and pass into solution again upon heating. The mixture thus obtained is distilled as described in Example 1. 3345 g of pure chloroacetyl chloride having a content of 1.34% by weight of dichloroacetyl chloride is taken overhead. The temperature in the bottoms rises to 120°C during the distillation. To maintain the level in the bottoms vessel bottoms product is continuously drained off through an outlet at the bottom and this solidifies on cooling. The total amount of bottoms product is 1666 g with a content of dichloroacetic acid of 4.64 percent. The difference in weight in the balance is accounted for by the escape of about 300 g of hydrogen chloride as offgas. Depletion of dichloroacetyl chloride in the distillate is calculated as 48.5 percent.

EXAMPLE 4

24,350 g of a mixture of 97.2% of chloroacetyl chloride and 2.3% of dichloroacetyl chloride as well as 0.5% of acetyl chloride is mixed with 250 g of methanol and subjected to continuous distillation at 80 mm as described in Example 1. A reflux ratio of 2:1 is maintained. In this way a total of 23,191 g of chloroacetyl chloride is distilled overhead which contains only 1.8% of dichloroacetyl chloride. The depletion is 22 and 93.5 percent of the amount introduced is rectified.

EXAMPLE 5

13,430 g of a mixture containing chloroacetyl chloride with 9.1% of dichloroacetyl chloride is mixed with 2% (270g) of propanol and distilled at 80 mm. 12,300 g of distillate is obtained with a dichloroacetyl chloride content of 6.41 percent which corresponds to a depletion of 30 percent. The rectification is 92 percent.

EXAMPLE 6

5% (600 g) of propanol is added to 12,170 g of a mixture having the same composition as in Example 5 and the mixture is continuously distilled at 80 mm. The temperature in the bottoms rises very quickly. 9830 g (81 percent) of distillate is obtained. The content of dichloroacetyl chloride is only 5.76 percent; this is equivalent to a depletion of 37 percent.

I claim:
1. A process for decreasing the amount of dichloroacetyl chloride contained in monochloroacetyl chloride which comprises treating monochloroacetyl chloride containing dichloroacetyl chloride with water, an alcohol or alkanediol of up to four carbon atoms or a fatty acid of up to four carbon atoms and separating the monochloro-acetyl chloride by distillation from the mixture thus obtained, the amount of water, alkanol, alkanediol or fatty acid is from 0.5 to 10 percent based on the monochloroacetyl chloride containing dichloroacetyl chloride.

2. A process as set forth in claim 1 wherein water is used as a treating agent.

3. A process as set forth in claim 2 in which the starting monochloroacetyl chloride contains up to 10% by weight of dichloroacetyl chloride.

4. A process as set forth in claim 2 wherein water is used in the stoichiometric amount based on the amount of dichloroacetyl chloride contained in the monochloroacetyl chloride.

5. A process as set forth in claim 2 wherein the distillation is carried out at a pressure of from 50 to 500 mm.

6. A process as set forth in claim 2 wherein a temperature of less than 130°C is maintained in the bottoms during the distillation.

* * * * *